United States Patent [19]

Spietschka et al.

[11] 4,456,762

[45] Jun. 26, 1984

[54] PROCESS FOR THE PREPARATION OF 4,7-DICHLORO-3-HYDROXY-THIONAPHTHENE

[75] Inventors: Ernst Spietschka, Idstein/Taunus; Manfred Urban, Wiesbaden, both of Fed. Rep. of Germany

[73] Assignee: Hoechst Aktiengesellschaft, Frankfurt am Main, Fed. Rep. of Germany

[21] Appl. No.: 383,731

[22] Filed: Jun. 1, 1982

[30] Foreign Application Priority Data

Jun. 3, 1981 [DE] Fed. Rep. of Germany ....... 3121980

[51] Int. Cl.$^3$ .......................................... C07D 333/52
[52] U.S. Cl. ..................................................... 549/56
[58] Field of Search ........................................ 549/56

[56] References Cited

U.S. PATENT DOCUMENTS 1,913,484  5/1931  Haller .................................... 549/56
2,158,032  5/1939  Lubs et al. ........................... 549/56

*Primary Examiner*—Alan Siegel
*Attorney, Agent, or Firm*—Curtis, Morris & Safford

[57] ABSTRACT

The invention provides a process for the preparation of 4,7-dichloro-3-hydroxy-thionaphthene by reaction of 2,5-dichlorophenyl-thioglycolic acid chloride in dichloromethane in the presence of Friedel-Crafts catalysts.

6 Claims, No Drawings

PROCESS FOR THE PREPARATION OF 4,7-DICHLORO-3-HYDROXY-THIONAPHTHENE

U.S. Pat. No. 2,158,032 discloses a process for the preparation of 4,7-dichloro-3-hydroxy-thionaphthene by cyclization of 2,5-dichlorophenyl-thioglycolic acid chloride in chlorobenzene at 60° C. in the presence of aluminum chloride as catalyst. The 4,7-dichloro-3-hydroxythionaphthene is further oxidized without intermediate isolation to yield the corresponding thioindigo. When copying this process with the intention of isolating pure 4,7-dichloro-3-hydroxy-thionaphthene it was observed that under these conditions chlorobenzene reacts with 2,5-dichlorophenyl-thioglycolic acid chloride and thus cannot be used as solvent for the intended purpose.

Other chlorinated hydrocarbons such as tetrachloro-ethane, ethylene chloride, perchloro-ethane, carbon tetrachloride or fluorochlorinated hydrocarbons likewise give 4,7-dichloro-3-hydroxy-thionaphthene with insufficient purity. Moreover, most of the aliphatic chlorinated hydrocarbons are anyhow unfit for this application because they cannot be regenerated except with great difficulty. Furthermore, the temperatures required in some cases for distilling off the solvents adversely affect the purity of the 4,7-dichloro-3-hydroxy-thionaphthene formed which is sensitive to heat.

Surprisingly, it has now been found that 4,7-dichloro-3-hydroxy-thionaphthene is obtained with the required high degree of purity and in very good yields by cyclization of 2,5-dichlorophenyl-thioglycolic acid chloride in the presence of Friedel-Crafts catalysts and of dichloromethane, which can be completely regenerated, as diluent.

The invention accordingly provides a process for the preparation of 4,7-dichloro-3-hydroxy-thionaphthenes by reaction of 2,5-dichlorophenyl-thioglycolic acid chloride in chlorinated hydrocarbons in the presence of Friedel-Crafts catalysts, which comprises carrying out the reaction at a temperature of from −20° to +40° C., preferably 0° to 30° C., especially 0° to 15° C., in dichloromethane.

Suitable Friedel-Crafts catalysts for the example aluminum bromide, especially aluminum chloride.

According to an especially preferred embodiment of the invention, 2,5-dichlorophenyl-thioglycolic acid chloride is added dropwise at 0° to 15° C. to a suspension of the aluminum halide in dichloromethane. Advantageously, from 1.2 to 1.4 mols of aluminum halide per mol of 2,5-dichlorophenyl-thioglycolic acid chloride are introduced into the reactor. For completing the reaction, it is recommended to continue intense intermixing of the batch by stirring at the temperature which was chosen for the dropwise addition.

After decomposition of the reaction mixture by means of ice/hydrochloric acid, the dichloromethane is advantageously separated by distillation and recycled to the process. The 4,7-dichloro-3-hydroxy-thionaphthene is suction-filtered and dried under reduced pressure.

According to the process of the invention, 4,7-dichloro-3-hydroxy-thionaphthene is obtained with a degree of purity which makes it excellently suitable for the manufacture of 4,4′, 7,7′-tetrachloro-thioindigo.

The following Examples illustrate the invention; parts and percentages being by weight unless otherwise stated. 2,5-dichlorophenyl-thioglycolic acid chloride and 4,7-dichloro-3-hydroxy-thionaphthene are designated as A and B, respectively.

EXAMPLE 1

51.1 Parts of A were added dropwise at 10°–15° C. within 3 hours to a suspension of 35 parts of anhydrous aluminum chloride in 100 parts of anhydrous dichloromethane. Stirring was continued at this temperature for 2 hours, the reaction mixture was subsequently poured onto a mixture of 160 parts of ice, 40 parts of water, 4 parts of concentrated hydrochloric acid and 0.4 parts of a 60% aqueous solution of a mixture of secondary alkanesulfonates (carbon chain distribution: $C_{13}$:<1%, $C_{13}$–$C_{15}$: about 58%, $C_{16}$–$C_{17}$: about 39%, >$C_{17}$:<3%), and the batch was stirred for a further half hour at 0° C. Subsequently, the dichloromethane was distilled off until a sump temperature of 70° C. was attained, the batch was suction-filtered, washed to neutral and dried at 50° C. and under reduced pressure of about 200 mbar. 44.5 Parts of a product containing 96.1% of B were obtained.

EXAMPLE 2

A was added dropwise at 0° C., and stirring was continued at this temperature until the reaction was complete. All other operations were as indicated in Example 1. 44.6 Parts of a product containing 97.1% of B were thus obtained.

EXAMPLE 3

A was added dropwise at 40° C., and stirring was continued at this temperature until the reaction was complete. All other operations were as indicated in Example 1. Thus, 43.7 parts of a product containing 93.2% of B were obtained.

EXAMPLE 4

51.1 Parts of A were added dropwise within 1 hour at 10°–15° C. to a suspension of 35 parts of anhydrous aluminum chloride in 100 parts of anhydrous dichloromethane. Stirring was continued at 10°–15° C. for 1 hour, and subsequently the reaction mixture was poured onto the mixture of ice, water, hydrochloric acid and alkanesulfonate as described in Example 1. All other operations were as indicated in Example 1. Thus, 44.4 parts of a product containing 94.8% of B were obtained.

EXAMPLE 5

1.1 Parts of A were added dropwise within 3 hours at 10°–15° C. to a suspension of 70 parts of anhydrous aluminum bromide in 100 parts of anhydrous dichloromethane. Stirring was continued for 2 hours at this temperature, and all other operations were as indicated in Example 1. Thus, 42.7 parts of a product containing 89.5% of B were obtained.

What is claimed is:

1. A process for the preparation of 4,7-dichloro-3-hydroxy-thionaphthene which comprises cyclizing 2,5-dichloro-phenyl-thioglycolic acid chloride at a temperature of from −20° to +40° C. in dichloromethane in the presence of a Freidel-Crafts catalyst.

2. The process as claimed in claim 1, which comprises adding dropwise 2,5-dichlorophenyl-thioglycolic acid chloride to a solution or suspension of the Freidel-Crafts catalyst in dichloromethane, and intensely intermixing the foregoing by stirring at the temperature chosen for the dropwise addition.

3. The process as claimed in claim 1, which comprises carrying out the reaction at a temperature of from 0° to 30° C.

4. The process as claimed in claim 1, which comprises carrying out the reaction at a temperature of from 0° to 15° C.

5. The process as claimed in claim 1, which comprises carrying out the reaction in the presence of aluminum chloride.

6. The process as claimed in claim 1, which comprises separating the dichloromethane after completed reaction and recycling it to the process.

* * * * *